United States Patent [19]

Nicks et al.

[11] Patent Number: 5,969,810
[45] Date of Patent: Oct. 19, 1999

[54] OPTICAL INSPECTION OF TRANSPARENT CONTAINERS USING TWO CAMERAS AND A SINGLE LIGHT SOURCE

[75] Inventors: Timothy J. Nicks; James A. Ringlien, both of Maumee, Ohio

[73] Assignee: Owens-Brockway Glass Container Inc., Toledo, Ohio

[21] Appl. No.: 09/078,507

[22] Filed: May 14, 1998

[51] Int. Cl.$^6$ .................................................. C01N 21/00
[52] U.S. Cl. ...................................... 356/239.4; 356/428
[58] Field of Search ............................... 356/239.4, 428; 256/223 B; 348/127

[56] References Cited

U.S. PATENT DOCUMENTS

| | | |
|---|---|---|
| 1,681,991 | 8/1928 | Littleton, Jr. . |
| 1,934,187 | 11/1933 | Glasgow et al. . |
| 3,963,348 | 6/1976 | Nakatani et al. . |
| 4,026,656 | 5/1977 | Kusz et al. . |
| 4,378,493 | 3/1983 | Dorf et al. . |
| 4,547,067 | 10/1985 | Watanabe . |
| 4,601,395 | 7/1986 | Juvinall et al. . |
| 4,736,851 | 4/1988 | Ricros et al. ........................ 356/239.4 |
| 4,919,534 | 4/1990 | Reed .......................................... 356/73 |
| 5,466,927 | 11/1995 | Kohler et al. . |
| 5,502,559 | 3/1996 | Powell et al. ............................. 356/73 |

*Primary Examiner*—Richard A. Rosenberger

[57] ABSTRACT

Apparatus for inspecting a container for variations that affect commercial acceptability of the container that includes a light source for directing diffuse polarized light energy through a container while the container is rotated about its axis. A first camera is disposed to receive diff-use polarized light energy transmitted from the light source through a portion of the container, so that the first camera receives an image of the container portion in which opaque variations appear dark against an otherwise bright background. A second camera receives light energy transmitted from the light source through substantially the same portion of the container, and includes a polarizer at cross-orientation to the polarizer at the light source. The second camera receives a bright image of stress variations in the container, which alter polarization of the diffuse polarized light energy passing through the container, against an otherwise dark background. An image processor is coupled to both of the cameras to scan associated images of the container portion viewed by the cameras for detecting and distinguishing between and among variations in the container.

15 Claims, 2 Drawing Sheets

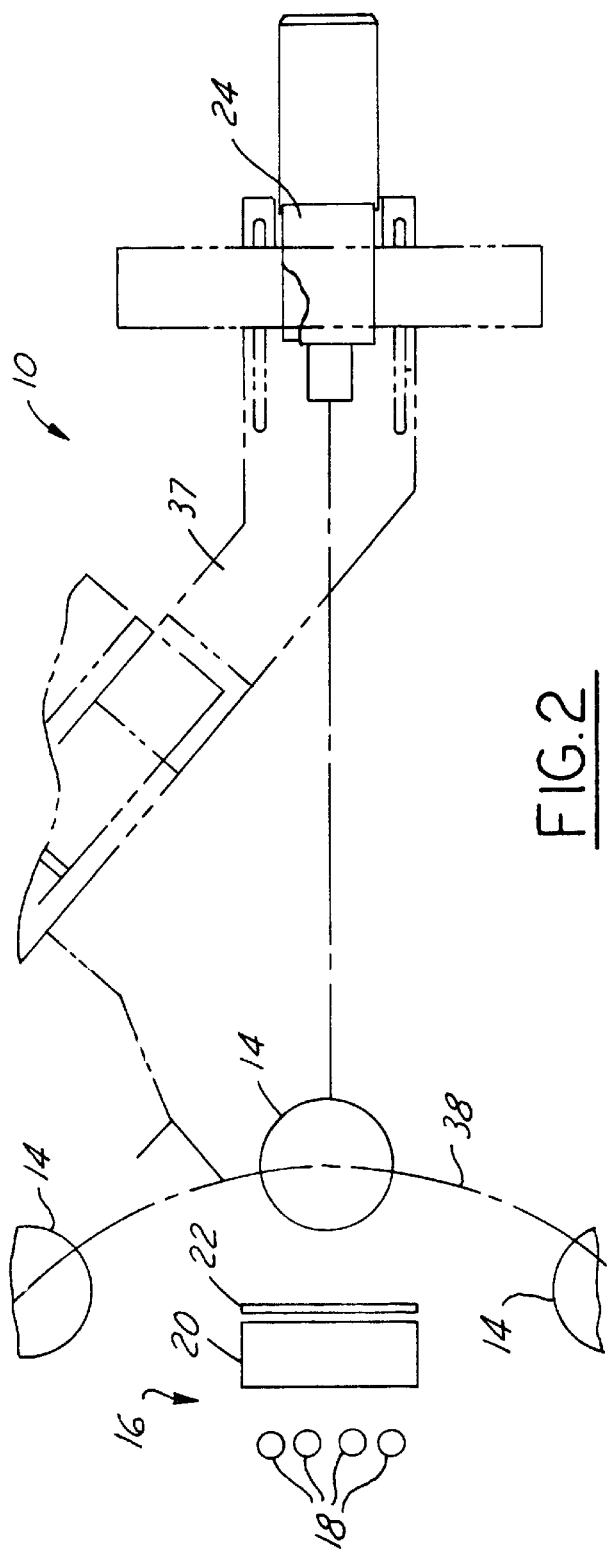

OPTICAL INSPECTION OF TRANSPARENT CONTAINERS USING TWO CAMERAS AND A SINGLE LIGHT SOURCE

The present invention is directed to inspection of transparent containers for commercial variations that affect the optical properties of the containers, and more particularly to a method and apparatus for inspecting containers for opaque and stress variations in the container at a single inspection station using a single light source.

BACKGROUND AND OBJECTS OF THE INVENTION

In the manufacture of transparent containers such as glass bottles and jugs, various types of anomalies can occur in the sidewalls, heels, bottoms, shoulders and/or necks of the containers. These anomalies, termed "commercial variations" in the art, can affect commercial acceptability of the containers. It has heretofore been proposed to employ electro-optical inspection techniques for detecting commercial variations that affect the optical properties of the containers. The basic principle is that a light source is positioned to direct light energy onto the container, and a camera is positioned to receive an image of the portion of the container illuminated by the light source. The light source may be of uniform intensity, or may be configured to have an intensity that varies across one dimension of the light source. Commercial variations in the portion of the container illuminated by the light source are detected as a function of light intensity in the image of the illuminated container received and stored at the camera.

U.S. Pat. Nos. 4,378,493, 4,378,494, 4,378,495 and 4,601,395, all of which are assigned to the assignee of the present application, disclose inspection techniques in which glass containers are conveyed through a series of positions or stations where they are physically and optically inspected. At one optical inspection station, a glass container is held in vertical orientation and rotated about its central axis. An illumination source directs diffuse light energy through the container sidewall. A camera, which includes a plurality of light sensitive elements oriented in a linear array parallel to the vertical axis of the container, is positioned to receive light transmitted through a vertical strip of the container sidewall. The output of each element in the linear array is sampled at increments of container rotation, and event signals are generated when the magnitude of adjacent signals differ by more than a preselected threshold. An appropriate reject signal is produced and the container is sorted from the conveyor line.

A problem is encountered in the manufacture of glass containers from recycled glass in that materials having different thermal expansion characteristics can become mixed in a single container. For example, it has been found that clear cookware, having very low thermal expansion characteristics, can become mixed with the glass for recycling. Any unmelted particles of the cookware that appear in the container create stress points on cooling that can fracture or become sites for later failures. Other inhomogeneities that can appear in the glass and cause stress variations include stones or bits of refractory material from the glass forehearth or spout. It is thus necessary to provide a method and system for detecting stress and opaque non-stress variations in the containers. However, space is limited in the existing inspection systems, and the various inspection stations in the systems in place cannot readily accommodate additional inspection apparatus.

It has heretofore been proposed to employ crossed polarizers for detecting stress variations in the sidewalls of containers. Light energy directed through the crossed polarizers, and through a container positioned between the crossed polarizers, normally presents a dark field at the imaging camera in the absence of stress variations in the container sidewalls. However, a stress variation alters polarization of the light energy passing through the container sufficiently to present a bright spot at the camera against the otherwise dark background, indicative of the stress variation. See U.S. Pat. No. 4,026,656, assigned to the assignee hereof, which discusses such technology by way of background, and which proposes to employ infrared light energy and infrared polarization filters to reduce the background effects of ambient light.

It is a general object of the present invention to provide a method and apparatus for inspecting transparent glass articles, particularly glass containers, for commercial variations that affect optical characteristics of the containers. A more specific object of the present invention is to provide a method and apparatus of the described character that are particularly well suited for detecting both stress variations and opaque variations (stress and non-stress) in the container. Another object of the present invention is to provide a method and apparatus of the described character for detection of stress and opaque non-stress variations in containers at a single inspection station, using a single light source. A further object of the present invention is to provide a method and apparatus of the described character that are economical to implement and reliable over an extended operating lifetime. Yet another object of the present invention is to provide a method and apparatus of the described character that are adapted to be implemented at a single inspection station of an existing container inspection system.

SUMMARY OF THE INVENTION

Apparatus for inspecting a container for variations that affect commercial acceptability of the container in accordance with a presently preferred embodiment of the invention includes a light source for directing diff-use polarized light energy through a container while the container is rotated about its axis. A first camera is disposed to receive diffuse polarized light energy transmitted from the light source through a portion of the container, so that the first camera receives an image of the container portion in which opaque variations appear dark against an otherwise bright background. A second camera receives light energy transmitted from the light source through substantially the same portion of the container, and includes a polarizer at cross-orientation to the polarizer at the light source. The second camera receives a bright image of stress variations in the container, which alter polarization of the diffuse polarized light energy passing through the container, against an otherwise dark background. An image processor is coupled to both of the cameras to receive associated images of the container portion viewed by the camera for detecting and distinguishing between and among variations in the container.

The first and second cameras each includes a linear array CCD sensor oriented in a direction coplanar with each other and with the axis of the container. The information processor scans the linear array sensors in the cameras at increments of container rotation to develop respective two-dimensional unwrapped images of the inspected portion of the container. Variations are detected and discriminated in response to a comparison of these two-dimensional images, by simultaneous display of the two-dimensional images for operator analysis and/or by automatic electronic comparison of the individual pixel signals in the images. The first camera in the preferred embodiment of the invention is diametrically opposed to the light source across the container, while the second camera is disposed beneath the first camera to view the container at an upward angle. The field of view of the second camera includes the container heel, at which stress variations that affect polarization of light energy can be particularly serious due to impact forces typically applied to the heel portion of the container during use. The light source in a preferred embodiment of the invention comprises a fluorescent source having high output in the visible range, preferably in the color temperature range of about 3000° to 5000° K. The invention may thus be readily implemented at a single station of an existing inspection system by placing the light source within the arc of travel of containers through the inspection system, and positioning the cameras on a system mounting bracket one above the other outside of such arc of travel.

BRIEF DESCRIPTION OF THE DRAWINGS

The invention, together with additional objects, features and advantages thereof, will be best understood from the following description, the appended claims, and the accompanying drawings in which:

FIG. 2 is a top plan view of the apparatus illustrated in FIG. 1; and

FIGS. 3A and 3B illustrate two-dimensional images of the container obtained employing the apparatus of FIGS. 1 and 2.

DETAILED DESCRIPTION OF PREFERRED EMBODIMENTS

Figure 1:
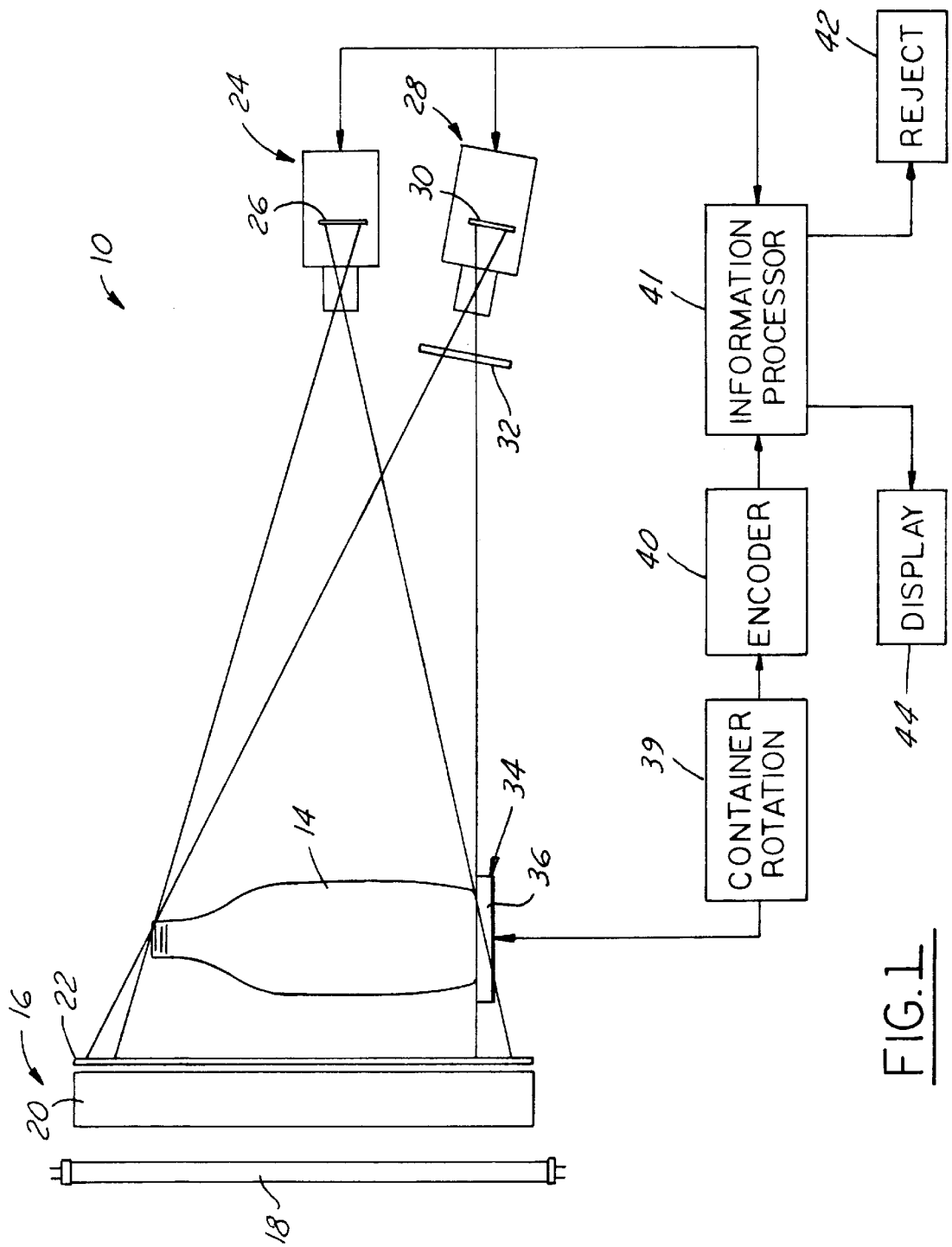
FIG. 1 is an electro-optical schematic diagram that illustrates an apparatus for detecting stress and opaque variations in containers in accordance with one presently preferred embodiment of the invention.

FIGS. 1 and 2 illustrate an apparatus 10 for inspecting a container 14 in accordance with one presently preferred embodiment of the invention. A light source 16 comprises one or more vertically oriented fluorescent lamps 18 that cooperate with a diffuser 20 to form a broad-area diffuse light source. Light energy is directed from diffuser 20 through a first polarizer lens 22 to a container 14. A first camera 24 is diametrically opposed to light source 16 across container 14, and contains a linear array CCD sensor 26 onto which is focused an opposing narrow strip of container 14 transilluminated by light source 16. A second camera 28 is positioned beneath camera 24 and contains a linear array CCD sensor 30, onto which the opposing narrow strip of container 14 transilluminated by light source 16 is focused through a second polarizer lens 32. Camera 28 thus views container 14 at a slight upward angle, which includes the heel of container 14. Polarizer lenses 22, 32 are cross-polarized with respect to each other. Linear array sensors 26, 30 are coplanar with each other, and coplanar with the axis of container 14. The linear dimensions of arrays 26, 30 are coplanar with each other and with the axis of container 14. The linear dimension of array 26 is parallel to the container axis, and the linear dimension of array 30 is at a slight angle to the container axis. Such angle will depend on heel curvature, and is preferably about 6°. Preferably, both cameras 24, 28 view a narrow strip of the container from heel to finish. It is currently preferred that light source 16 include one or more fluorescent lamps 18 for generating light in the visible portion of the light spectrum, as contrasted with incandescent light sources typical in the prior art. Polarizer lenses for white light are typically much less expensive than polarizers for infrared or near-infrared light generated by incandescent light sources. Bulb 18 in the preferred embodiment of the invention comprises one or more high output bulbs in the visible light range. There is a trade-off between the response characteristics of sensors 26, 30, which typically are more sensitive in the infrared range, and expense associated with polarizer lenses 22, 32, which are less expensive in the visible range. A light source color temperature range of about 3000° to 5000° K. is presently preferred, with a color temperature of 3000° K. being particularly preferred.

A conveyor 34, typically including a starwheel (not shown) and a slide plate 36, is disposed and connected to a source of containers so as to move the successive containers through an arcuate path 38 (FIG. 2) and bring the successive containers into position at apparatus 10, which is disposed at one station of a starwheel-conveyor container inspection system. Conveyor 34 and the overall inspection system may be of any suitable type, such as those shown in U.S. Pat. Nos. 4,230,319 and 4,378,493, the disclosures of which are incorporated herein by reference for purposes of background. Cameras 24, 28 are adjustably mounted one above the other on a camera mounting bracket 37 that extends outwardly from conveyor 34. Successive containers are held in fixed position between light source 16 and cameras 24, 28, and are rotated by a drive roller 39 or the like about the central axis of the container. An encoder 40 is coupled to the container rotation mechanism to provide signals indicative of increments of container rotation. Such increments may comprise either fixed angular increments of rotation, or fixed time increments of rotation at constant velocity. An information processor 41 is coupled to encoder 40 and to camera 24, 28 for scanning sensors 26, 30 at increments of container rotation, and developing corresponding two-dimensional electronic images of container 14. These two-dimensional images are formed in one dimension by the signals from successive elements of the respective linear array sensors, and in the second dimension by the increments of container rotation.

In operation, successive containers 14 are brought into position by conveyor 34 between light source 16 and cameras 24, 28. The container is then held in fixed position and rotated about its central axis. Diffuse and polarized light energy from light source 16 is directed through container 14 onto array 26 of camera 24, which thus forms a bright background image. Any opaque variations in the container will block or absorb transmission of light energy from light source 16 to camera array 26, so that such opaque variations form dark images against an otherwise bright background. (The term "opaque" variations encompasses not only variations that block or absorb light energy, but also refractive variations that are of such a size as effectively to refract light energy transmitted therethrough away from camera 24 and reflective variations that reflect the light energy away from the camera. In other words, a variation that blocks or absorbs light energy at the container, a variation that refracts the light energy away from the camera, and a variation that reflects light energy away from the camera, will all appear at array 26 of camera 24 as a dark image against an otherwise bright background.) At the same time, the polarized diffuse light energy from light source 16 is transmitted through container 14 to polarizer 32 in front of camera 28. The crossed orientations of polarizer lenses 22, 32 normally create at array 30 of camera 28 a dark background or field. However, any variations in container 14, such as stress variations in the container sidewall, which alter polarization of the light energy transmitted therethrough, will appear at array 30 of camera 28 as a bright image against an otherwise dark field or background.

FIGS. 3A and 3B illustrate unwrapped two-dimensional images of a container 14 scanned by information processor 41 from cameras 24, 28 respectively during one revolution of the container. For example, a non-stress producing stone is indicated by a dark image 50 in FIG. 3A, and no corresponding image at the same x-y position in FIG. 3B. A stress-producing stone is indicated by a dark image 52*a* in FIG. 3A, and a corresponding dark image 52*b* in FIG. 3B surrounded by a bright image 52*c* of the area of stress surrounding the stone. The images 50, 52*a* indicate dimensions of the stones. A bright image 54 in FIG. 3B, coupled with the absence of an image at the corresponding location of FIG. 3A, may indicate a stress variation produced by inclusion of a piece or particle of transparent cookware having similar transparency characteristics but differing thermal characteristics from those of surrounding glass in the container sidewall. The elongated bright image 56 in FIG. 3B against an otherwise dark background may indicate devitrification in the container sidewall. Stress-producing variations in the container may be indicative of areas of weakness in the container that might be subject to fracture as a result of impact during normal handling of the container, or as a result of thermal stress when the container is filled or handled. The heel portion of the container—i. e., the portion of the container that joins the container sidewall to the container bottom—is particularly sensitive to inclusion of stress variations because the heel portion of the container is subjected to stress and impact during normal use. Thus, a particularly important advantage of the apparatus of the invention as illustrated in FIG. 1 lies in the fact that camera 28 views container 14 at a slight upward angle that includes the entire heel portion of the container.

Information processor 41 is coupled to a display 44 for simultaneously displaying to an operator the unwrapped two-dimensional images (e.g., FIGS. 3A and 3B) generated from camera 24, 28. The operator may analyze the information so displayed, and implement appropriate corrections in the manufacturing cycle. Alternatively or simultaneously, information processor 41 may automatically electronically compare the two-dimensional images by appropriate pixel comparison techniques, to implement automatic correction of the manufacturing process (see, for example, U.S. Pat. No. 4,762,544) and/or activate a mechanism 42 for rejecting or removing an unsatisfactory container from the conveyor line. It is also advantageous not to recycle containers having stones, as the stones may recur in new containers formed from the recycled glass. The information provided by the present invention can be used to give more accurate indications of reject containers that should not be recycled. Provision of two unwrapped two-dimensional images for analysis, with the images being obtained by differing optical techniques responsive to differing types of variations, provides enhanced opportunity for classification of the variations—e.g., size, shape and stress or non-stress. The image processor can readily classify the type of variation, such as stressed stone, non-stressed stone, viscous knot, blister, ribbon tear, dope, etc.

There have thus been provided in accordance with the present invention a method and apparatus for inspecting glass articles such as containers for commercial variations that affect the optical characteristics of the containers, particularly stress variations and opaque variations in the containers. The method and apparatus of the invention may be implemented employing relatively inexpensive polarizer material responsive to light energy in the visible region. The techniques of the invention may be readily employed in connection with both clear (flint) and colored (e.g., amber) glass. The method and apparatus of the invention may be implemented at a single station in a container inspection system, employing a single light source, and may be readily retrofitted into existing starwheel-type and other container inspection systems.

We claim:

1. Apparatus for inspecting a container for variations that affect commercial acceptability of the container, comprising:
   means for rotating a container about its axis,
   a light source, including a diffuser and a polarizer, for directing diffuse polarized light energy through a container in said rotating means,
   a first camera disposed with respect to said rotating means to receive diffuse polarized light energy transmitted from the light source through a portion of the container, so that said first camera receives an image of said container portion in which opaque variations appear dark against an otherwise bright background,
   a second camera disposed with respect to said rotating means to receive light energy transmitted from said light source through substantially the same said portion of the container, and including a second polarizer at cross orientation to said first polarizer so that said second camera receives a bright image of stress variations in the container portion that alter polarization of the diffuse polarized light energy passing therethrough against an otherwise dark background, and
   an image processor coupled to both of said first and second cameras for receiving associated images of said container portion, including means for detecting and discriminating between variations in the container as a function of a comparison between said first and second images.

2. The apparatus set forth in claim 1 wherein said detecting and discriminating means comprises means for automatically comparing said images to each other pixel by pixel.

3. The apparatus set forth in claim 2 wherein said first and second cameras each includes a linear array CCD sensor oriented in a direction coplanar with each other and with the axis of the container in said rotating means.

4. The apparatus set forth in claim 3 wherein said information processor includes means for scanning said linear array sensors in said cameras at increments of container rotation to develop respective two-dimensional images of said container portion, and where said means for detecting and discriminating between variations is responsive to a comparison of said two-dimensional images.

5. The apparatus set forth in claim 4 wherein said detecting and discriminating means comprises an operator display at which an operator can view said two-dimensional images simultaneously.

6. The apparatus set forth in claim 4 wherein said first camera is diametrically opposed to said light source across the container and in which the linear array sensor is parallel to the axis of the container, and wherein said second camera is disposed beneath said first camera to view the container at an upward angle.

7. The apparatus set forth in claim 6 wherein said portion of the container viewed by said second camera includes the container heel.

8. The apparatus set forth in claim 7 wherein both of said cameras view substantially the entire container from heel to finish.

9. The apparatus set forth in claim 7 wherein said means for rotating the container comprises a conveyor for indexing a series of containers through an arc, with said light source being disposed within said arc and said cameras being disposed outside of said arc, and for holding each container in turn in stationary position between said light source and said cameras and rotating the container about its axis.

10. The apparatus set forth in claim 1 wherein said light source comprises a fluorescent light source.

11. The apparatus set forth in claim 10 wherein said fluorescent light source has a color temperature in the range of about 3000° K. to about 5000° K.

12. A method of inspecting a container for variations that affect commercial acceptability of the container comprising the steps of:

(a) directing light energy from a light source through the container toward first and second cameras simultaneously, (b) receiving at said first camera an image of a portion of the container in which opaque variations appear dark against a bright background, (c) receiving at said second camera an image of the same said portion of the container in which stress variations appear bright against an otherwise dark background, and (d) detecting opaque and stress variations in the container as a function of a comparison between said images from said first and second cameras.

13. The method set forth in claim 12 comprises the additional step of: (e) rotating the container about its axis, and wherein said step (d) includes the step of scanning said cameras at increments of container rotation.

14. The method set forth in claim 13 wherein said steps (a) and (c) include the step of positioning crossed polarizers at said light source and said second camera.

15. The method set forth in claim 12 in which said comparison in said step (d) is carried out pixel by pixel between said images.

* * * * *